United States Patent [19]

Brady et al.

[11] 4,301,025
[45] Nov. 17, 1981

[54] DERIVATIVES OF POLYPHOSPHORIC ACID PARTIAL ESTERS

[75] Inventors: Thomas P. Brady, Holliston; Horst G. Langer, Wayland, both of Mass.

[73] Assignee: The Dow Chemical Company, Midland, Mich.

[21] Appl. No.: 119,064

[22] Filed: Feb. 6, 1980

[51] Int. Cl.³ .............................................. C23F 11/16
[52] U.S. Cl. .......................... 252/389 A; 106/14.12; 106/14.21; 106/15.05; 106/18.17; 252/8.55 E; 252/68; 252/75; 252/78.5; 260/429.9; 260/430; 260/438.1; 260/438.5 R; 260/439 R; 260/448 R; 260/933; 422/15
[58] Field of Search .............. 252/389 A, 8.55 E, 68, 252/75, 78.5; 260/429.5, 429.9, 430, 438.1, 438.5 R, 439 R, 448 R, 933; 106/14.12, 14.21, 15.05, 18.17; 422/15

[56] References Cited

U.S. PATENT DOCUMENTS

| | | | |
|---|---|---|---|
| 3,062,858 | 11/1962 | Cramer et al. | 260/933 |
| 3,150,039 | 9/1964 | Lanham et al. | 260/933 |
| 3,757,864 | 9/1973 | Crawford et al. | 252/8.55 R |
| 4,062,687 | 12/1977 | Maurie et al. | 106/18.17 |
| 4,083,860 | 4/1978 | Ruf | 260/429.7 |
| 4,089,651 | 5/1978 | Scott | 252/8.55 E |
| 4,148,782 | 4/1979 | Maurie et al. | 106/15.05 |
| 4,154,691 | 5/1979 | Maurie et al. | 106/15.05 |

FOREIGN PATENT DOCUMENTS 2013643 8/1979 United Kingdom .

OTHER PUBLICATIONS

Roseman et al., Jour. of the A.C.S., vol. 83 (1961), pp. 659–663.
Nussbaum et al., Tetrahedron, vol. 20 (1964), pp. 2467–2472.
Chem. Pharm. Bull. Japan, Furukawa et al., vol. 13 (1965), pp. 16–21.
Kochetkov et al., Tetrahedron, vol. 19 (1963), pp. 1207–1218.

*Primary Examiner*—Benjamin R. Padgett
*Assistant Examiner*—Irwin Gluck
*Attorney, Agent, or Firm*—Douglas N. Deline

[57] ABSTRACT

Derivatives of polyphosphoric acid partial esters of the formula

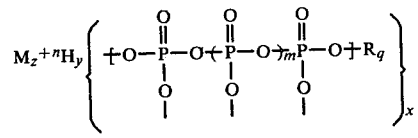

wherein R is the remnant of a (poly)glycol monoether, phenol or alkanol provided that in at least one occurrence R is the remnant of a (poly)glycol monoether, and M is a positive counterion of valence n are disclosed.

4 Claims, No Drawings

DERIVATIVES OF POLYPHOSPHORIC ACID PARTIAL ESTERS

BACKGROUND OF THE INVENTION

Known in the past have been certain metal ore extractants for use in aqueous systems for removing metal values. The compounds, disclosed in U.S. Pat. Nos. 2,866,680 and 2,947,774, are certain dialkyl esters of diphosphoric acid wherein the alkyl moiety is the remnant of an alkanol. The references teach that the compounds rapidly decompose, most likely forming monophosphate esters.

SUMMARY OF THE INVENTION

According to the instant invention are provided derivatives of polyphosphoric acid partial esters of the formula

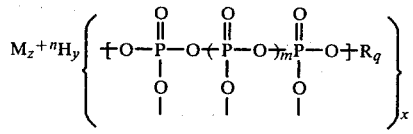

wherein
R is each occurrence a remnant formed by removal of a hydroxyl from a monohydroxyl compound selected from:
(a) a (poly)alkylene glycol, monoether of the formula

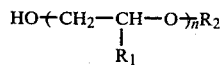

wherein $R_1$ is hydrogen, methyl, or halomethyl; $R_2$ is $C_{1-6}$ alkyl or haloalkyl, phenyl, halophenyl or methylphenyl; and n is an integer from 1 to 4;
(b) a phenol or halophenol; or
(c) a $C_{1-20}$ aliphatic or halogenated aliphatic compound;
provided that in at least one occurrence R is a remnant of (a);
M is independently each occurrence an ammonium, substituted ammonium, or metal cation having valence n;
m is an integer from zero to three; y is an integer equal to or greater than zero; and q, x and z are all integers greater than or equal to one selected such that $(z.n)+y=x(m+4-q)$ and $q \leq m+3$.

The monoethers of (poly)alkylene glycols of the previously described formula suitably include for example methyl, ethyl, propyl, n-butyl or tertiary-butyl ethers of ethylene glycol, propylene glycol, (poly)ethylene or (poly)propylene glycols.

The phenol or halophenols include for example mono- and polyhalogenated phenols such as chloro- and bromophenols.

The $C_{1-20}$ aliphatic monohydroxyl compounds include common alkanols and halogenated derivatives thereof and unsaturated monohydroxyl compounds such as hydroxy-substituted alkenes, alkynes and halogenated derivatives thereof.

Preferred are the compounds having a ratio of monohydroxyl compound remnant to phosphorus (R:P) of about 1:1, that is, compounds of the above formula wherein q equals m+2. Particularly preferred are (poly)alkylene glycol monoether derivatives of the diesters of diphosphoric acid, that is, compounds of the above formula wherein m is zero, R is selected from (a) and q is two.

The compounds are useful as corrosion inhibitors for functional fluids such as heat and pressure transmission fluids and as fire retarding agents for cellulosic materials.

DETAILED DESCRIPTION OF THE INVENTION

The invented compounds are ammonium or metal-containing derivatives of partial esters of polyphosphoric acids.

By "ammonium" is meant not only the monovalent cationic derivative of ammonia formed by addition of a hydrogen ion thereto, but also $C_{1-20}$ aliphatic and aromatic amine derivatives formed in a similar manner by addition of a hydrogen ion to the respective amine compounds. Included are primary, secondary and tertiary amines.

The metal employed is not critical and such may be selected from alkali metal and alkaline earth metal elements, the transition elements and the elements of group 3a of the periodic table. Preferred are Al, Ti, Cr, Mn, Fe, Co, Ni, Cu, Zn and Ag. Especially preferred are Al and Fe. The electronic state of the metal species is not fully understood and the compounds in many ways exhibit the qualities of coordination complexes.

The compounds may be formed by reaction of certain hereinafter-described partial esters of polyphosphoric acid with ammonia or amines, ammonium or substituted ammonium hydroxides, halides, carbonates or oxides as well as with the above-described neutral metals or their corresponding metal oxides, carbonates, hydroxides, halides, sulfates or nitrates. Mixtures of reactants and successive reactions of the partial esters with combinations of the above reactants, e.g., first reaction with a metal salt followed by neutralization of remaining acid functionality with ammonia or amine compounds may also be employed. In such compounds both ammonium and the above-described metal ion species are present.

The partial esters of polyphosphoric acid useful in forming the compounds of the present invention are of the formula

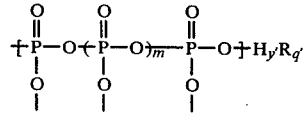

wherein R and m are as previously defined; and y' and q' are integers greater than or equal to one such that $y'=(m+4)-q'$.

The ratio of monohydroxyl compound remnant to phosphorus in the reaction product is desirably about 1:1.

These partial esters of polyphosphoric acid may be formed by the reaction of a (poly)alkylene glycol monoether optionally in combination with the phenol, halogenated phenol or $C_{1-20}$, aliphatic or halogenated aliphatic monohydroxyl compounds with phosphorus pentoxide. Alternatively the monohydroxyl compounds may be reacted in sequence. Remnant acid functionality is assured by reacting a stoichiometrically limited amount of the monohydroxyl compounds. Preferably in order to assure the presence of at least some (poly)alkylene glycol monoether remnant in each molecule of the reaction product, at least one-quarter mole of (poly)alkylene glycol monoether is reacted with each mole of $P_2O_5$. The reaction technique is well-known being similar to that disclosed in U.S. Pat. No. 2,866,680. Accordingly the monohydroxyl reactant is controllably added to a slurry comprising phosphorus pentoxide and an organic solvent such as the lower alkanes, aromatics or halogenated hydrocarbons. A preferred solvent is dichloromethane.

The exothermic reaction causes heating of the reaction mass. Proper choice of a solvent allows the reaction to be maintained at a gentle reflux at moderately elevated temperatures. The reaction may be continued for several hours or longer until the $P_2O_5$ is substantially completely reacted. Additional heating during the course of the reaction may be accomplished by conventional means.

The product, generally a light colored liquid, may be separated from any excess unreacted $P_2O_5$ by decanting or filtration, and the solvent removed if desired by evaporation or other technique.

Reaction of the partial esters of polyphosphoric acid with the previously described ammonia, amine or metal reactants is accomplished by contacting the two reactants optionally in the presence of an inert solvent which may be the solvent previously used for formation of the partial ester. Elevated temperatures may also be employed to increase the rate of reaction.

The resulting compounds are easily recovered in high purity by evaporation of the reaction solvent. Monophosphate contaminants are produced only in minor proportions during the reaction and are preferably present in an amount less than 10 percent by weight. Generally a mixture of the desired compounds is produced. The metal-containing compounds are believed to exist as metal coordination complexes, having the empirical formulas previously stated. Assignment of more definitive structural formulas to the various compounds cannot be attempted at the present time since the compounds exist as an intricate coordination network, a composition comprised primarily of the above-defined coordination complexes in which the charged species are mobile or capable of interchanging positions, which is randomly oriented in three dimensions. While such a network is referred to herein as a derivative of polyphosphoric acid partial esters, it is understood that within the network some monophosphate species may also be said to exist. Preferably such monophosphate species comprise 10 percent or less by weight of the coordination network.

The compounds have been found to be useful corrosion inhibitors for use in functional fluids such as mechanical pressure transmission fluids, heat transfer fluids, metal cutting fluids and the like. More particularly the compounds of the invention have been found to effectively inhibit the corrosion of aluminum and iron and iron-containing metals such as steel or cast iron in the presence of functional fluids comprising water. It is also desirable to add the invented compounds to fluids which initially contain no water but are subject to possible water contamination during use.

Advantageously the compounds are combined with the remaining components of the functional fluid in minor proportions from about 0.1 to about 10 percent by weight.

SPECIFIC EMBODIMENTS

The following examples are included as illustrative of the present invention and are not to be construed as limiting.

EXAMPLE 1

To a reaction flask containing 500 ml $CH_2Cl_2$ under nitrogen atmosphere, phosphorus pentoxide (270 g, 1.9 moles) was added with stirring. Over approximately 2 hours, 2-n-butoxyethanol (425 g, 3.6 moles reagent grade) was added from a dropping funnel, causing a gentle reflux to occur. After complete addition only a small amount of unreacted $P_2O_5$ remained. The flask contained a clear yellow colored solution. Reaction for an additional 24 hours resulted in complete conversion of $P_2O_5$ and a darker colored solution. Analyses by $^{31}P$ nuclear magnetic resonance spectroscopy indicated the product comprised greater than 90 percent of the diphosphoric acid half ester with minor amounts of other partial esters of polyphosphoric acids plus monophosphates and full ester contaminants.

EXAMPLE 2

A portion of the solution produced in Example 1 was added to a glass reaction vessel. Aluminum turnings were added a small amount at a time. Initial reaction was induced by adding a trace of water and heating to a temperature of about 148° C. After initiation of the reaction, more aluminum turnings were added and reacted until further hydrogen evolution ceased.

The viscous liquid reaction solution was decanted. Evaporation of the $CH_2Cl_2$ solvent left a white crystalline solid identified as the desired product by nuclear magnetic resonance spectroscopy.

EXAMPLE 3

A portion of the product produced in Example 1 was neutralized by bubbling dry $NH_3$ into the reaction mixture at a rate sufficient to cause a gentle reflux. After about 90 minutes no further exotherm occurred indicating that the reaction was complete.

EXAMPLE 4

The reaction conditions of Example 1 was repeated except that the glycol ether utilized was 1-methoxy-2-propanol added to $P_2O_5$ in a molar ratio of about 1.9:1. The product recovered was primarily the diester of diphosphoric acid having the empirical formula $H_2P_2O_5(O-CH(CH_3)CH_2OCH_3)_2$.

EXAMPLE 5

Potassium hydroxide (16.8 g, 0.3 mole) was dissolved in 20 ml water. To this solution was added 1-methoxy-2-propanol (200 g). The mixture was rapidly stirred while the diester of diphosphoric acid prepared in Example 4 (48.3 g, 0.15 mole), was slowly added. A clear homogeneous yellowish colored reaction mixture resulted containing 24.6 percent by weight of the alkali metal salt of the above diester of diphosphoric acid.

EXAMPLE 6

The composition prepared in Example 5 was tested as an iron corrosion inhibitor. Testing was conducted according to the experimental procedure outlined in American Society of Testing Methods D-1384 glassware corrosion test. Accordingly, two solutions, one containing known corrosion-inhibiting compounds the other the compound of Example 5, were prepared for comparison purposes. In both cases the base component consisted of a solution of 50 percent 1-methoxy-2-propanol and 50 percent deionized water. Formulation data and test results are contained in Table I.

TABLE I

| Fluid 1 | | Fluid 2 | |
|---|---|---|---|
| base fluid inhibitors | 99.4% | base fluid inhibitor | 98.0% |
| NaNO$_2$ | 0.5% | Example 5 | 2.0% |
| tolyl triazole | 0.1% | | |

| Test Results | |
|---|---|
| Wt. loss Fluid 1 (mg) | Wt. loss Fluid 2 (mg) |
| Copper 1.2 | 4.3 |
| Aluminum 5.4 | 3.9 |
| Steel 5.2 | 1.4 |
| Iron 642.3 | 5.2 |

We claim:
1. A composition of matter consisting essentially a compound of the formula

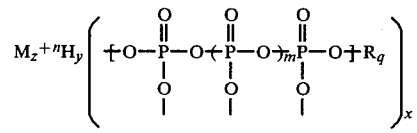

wherein

R is each occurrence a remnant formed by removal of a hydroxy from a monohydroxyl compound selected from:
(a) a (poly)glycol monoether of the formula

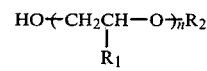

wherein $R_1$ is hydrogen, methyl or halomethyl; $R_2$ is $C_{1-6}$ alkyl or haloalkyl, phenyl, halo-phenyl or methylphenyl; and n is an integer from 1 to 4;
(b) a phenol or halophenol; and
(c) a $C_{1-20}$ aliphatic or halogenated aliphatic monohydroxyl compound; provided that in at least one occurrence R is a remnant of (a);
M is independently each occurrence an ammonium or substituted ammonium ion or a metal ion having valence n;
m is an integer from zero to three; y is an integer equal to or greater than zero; and q' x and z are all integers greater than or equal to one selected such that (z·n)+y=x(m=4=q) and q≦m+3 and no more than 10 percent by weight of monophosphate esters or partial esters.
2. The composition of claim 1 wherein R is each occurrence selected from (a).
3. A composition of claim 1 wherein M is sodium.
4. A process for inhibiting corrosion of aluminum- or iron-containing metals in contact with a functional fluid comprising adding to the functional fluid a corrosion-inhibiting amount of a composition of claim 1 or 3.

* * * * *

UNITED STATES PATENT AND TRADEMARK OFFICE
CERTIFICATE OF CORRECTION

PATENT NO. : 4,301,025

DATED : November 17, 1981

INVENTOR(S) : Thomas P. Brady and Horst G. Langer

It is certified that error appears in the above—identified patent and that said Letters Patent is hereby corrected as shown below:

Col. 1, line 51, "(z.n)" should read -- (z·n) --.

Col. 4, line 45, "was repeated" should read -- were repeated --.

Col. 5, line 23, Claim 1, line 1, "essentially a" should read -- essentially of a --.

Col. 6, line 2, Claim 1, line 6, "hydroxy" should read -- hydroxyl --.

Signed and Sealed this

Eleventh Day of May 1982

[SEAL]

Attest:

GERALD J. MOSSINGHOFF

Attesting Officer

Commissioner of Patents and Trademarks